(12) United States Patent
Kiser et al.

(10) Patent No.: US 6,395,227 B1
(45) Date of Patent: May 28, 2002

(54) TEST STRIP FOR MEASURING ANALYTE CONCENTRATION OVER A BROAD RANGE OF SAMPLE VOLUME

(75) Inventors: Ernest J. Kiser, Los Altos; Deborah P. Tuohy, San Jose, both of CA (US); John M. Dubowik, Buzzard's Bay, MA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 08/442,035

(22) Filed: May 16, 1995

Related U.S. Application Data

(63) Continuation-in-part of application No. 07/960,579, filed on Oct. 13, 1992, now Pat. No. 5,418,142, which is a continuation of application No. 07/691,192, filed on Apr. 25, 1991, now abandoned, which is a continuation of application No. 07/399,055, filed on Aug. 28, 1989, now abandoned, and a continuation-in-part of application No. 07/736,537, filed on Jul. 26, 1991, now Pat. No. 5,306,623.

(51) Int. Cl.⁷ .............................................. G01N 21/00
(52) U.S. Cl. .............................. 422/56; 422/57; 435/14
(58) Field of Search ........................ 422/56, 57; 435/14

(56) References Cited

U.S. PATENT DOCUMENTS

| | | | | |
|---|---|---|---|---|
| 3,690,836 A | * | 9/1972 | Buissiere et al. | 23/253 TP |
| 4,761,381 A | * | 8/1988 | Blatt et al. | 436/165 |
| 5,234,813 A | * | 8/1993 | McGeehan et al. | 435/7.9 |
| 5,306,623 A | * | 4/1994 | Kiser et al. | 435/14 |
| 5,411,858 A | * | 5/1995 | McGeehan et al. | 435/4 |
| 5,418,142 A | * | 5/1995 | Kiser et al. | 435/14 |
| 5,451,350 A | * | 9/1995 | Macho et al. | 264/442 |

\* cited by examiner

*Primary Examiner*—Ralph Gitomer

(57) ABSTRACT

A test strip for determining the concentration of an analyte in a body fluid includes a membrane in fluid communication with a porous layer. The membrane and the porous layer are divided into compressed portions, which restrict the capillary flow of the body fluid, and uncompressed portions. The uncompressed portions are adapted to absorb and retain body fluids in excess of the amount required for operation of the test strip. The test strip may be constructed with an internal relief chamber to accommodate the uncompressed portions. A method of making the test strip by pressure and/or heat sealing individual components on a shaping die is also provided.

17 Claims, 4 Drawing Sheets

TEST STRIP FOR MEASURING ANALYTE CONCENTRATION OVER A BROAD RANGE OF SAMPLE VOLUME

CROSS-REFERENCE TO RELATED APPLICATIONS

This application is a continuation-in-part of copending U.S. application Ser. No. 07/960,579, filed Oct. 13, 1992, now U.S. Pat. No. 5,418,142 which is a continuation of U.S. application Ser. No. 07/691,192, filed Apr. 25, 1991, abandoned, which is a continuation of U.S. application Ser. No. 07/399,055, filed Aug. 28, 1989, abandoned, and is a continuation-in-part of U.S. application Ser. No. 07/736,537, filed Jul. 26, 1991, now U.S. Pat. No. 5,306,623.

BACKGROUND OF THE INVENTION

1. Field of the Invention

The present invention relates to a test strip which allows a user to determine the concentration of an analyte in a liquid test sample. The test strip includes an absorbent membrane and a reagent that undergoes a change in color when exposed to the analyte, such as glucose or cholesterol, in a body fluid.

2. Description of Related Art

Test strips are commonly used for determining the concentration of analytes in liquid test samples. For example, known test strips can detect glucose, cholesterol, proteins, ketones, uric acid, phenylalanine, or enzymes in body fluids, such as blood or urine. The operation of such test strips has become so simple and reliable that the test strips can be used by patients to determine their own analyte concentrations.

Many test strips require a user to apply a drop of a body fluid to a reagent pad, or to a transport medium which conducts the fluid to the reagent pad, where an oxidizable dye or other indicator changes color to signal the presence of the analyte. It is sometimes difficult to bring exactly the right amount of body fluid to the test strip. If too little fluid is delivered, the test strip may not function properly. If too much fluid is applied to the test strip, excess fluid may drip from the test strip. Unnecessary contact between the user and the body fluid, which is typically blood, urine, or saliva, is preferably avoided.

SUMMARY OF THE INVENTION

The invention is directed to a color-indicating test strip which operates with a relatively small volume of body fluid but is capable of absorbing and retaining several times the required volume of body fluid, thereby minimizing any tendency for the body fluid to drip from the test strip. The test strip includes a membrane containing a color-changing reagent in contact with a porous sheet that has a pillow portion adapted to absorb excess body fluid from the membrane. The membrane extends across and protrudes into a window in the test strip. The window serves both to make visible any color change and to allow oxygen access to the membrane. The pillow portion is located in a protective channel defined by a relatively rigid container. The test strip is small, inexpensive, and suitable for mass production by heat-sealable packaging methods.

In one aspect, the invention is a test strip that comprises:

a cover sheet, having an elongated window cut through it;

a lamellar membrane adjacent to the cover sheet, extending across and into the window and containing a reagent tat reacts with the analyte to produce a color change;

a porous sheet in fluid communication with the membrane, having a pillow portion and a compressed portion, the pillow portion being substantially aligned with the window; and a backing sheet, adjoining the porous sheet and having a sample port cut through it;

whereby fluid introduced into the sample port can flow to the membrane, and analyte in the fluid can react with the reagent to produce a color change visible through the window.

In another aspect, the invention is a test strip comprising a backing sheet. An opening through the backing sheet leads to an absorbent sheet of a relatively compressible nonwoven material, so that a liquid that passes through the opening is absorbed in the absorbent sheet. The absorbent sheet is sandwiched between the backing sheet and a relatively incompressible planar center plate. Because a central part of the center plate has been removed, as by punching, the center plate extends around an internal relief chamber. One of the faces of the center plate is fastened to the absorbent sheet. The other face of the center plate is attached to one side of a generally planar permeable membrane that has been treated with a reagent capable of changing color on contact with an analyte in a liquid solution. The side of the membrane is held by the face of the center plate, so that a portion of the membrane extends across and protrudes into the internal relief chamber of the center plate. A cover sheet defines a window that is generally parallel to and has a cross section which is approximately the same size as the internal relief chamber. The cover sheet is bound against the other side of the membrane with the portion of the membrane that is visible through the window bulging into the window.

The invention also provides a method of making a test strip. The cover sheet with the heat-sealable coating, the membrane, the porous layer, the adhesive, and the backing sheet are stacked as a heat-sealable package on a heatable shaping die. The die is generally flat, but has a groove adapted to accommodate the uncompressed porous layer in a region that is aligned with the window. The die is heated and forced against the package to compress portions of the membrane and porous layer and to bond the cover sheet and backing sheets in place.

DETAILED DESCRIPTION OF THE PREFERRED EMBODIMENT

Figure 1:
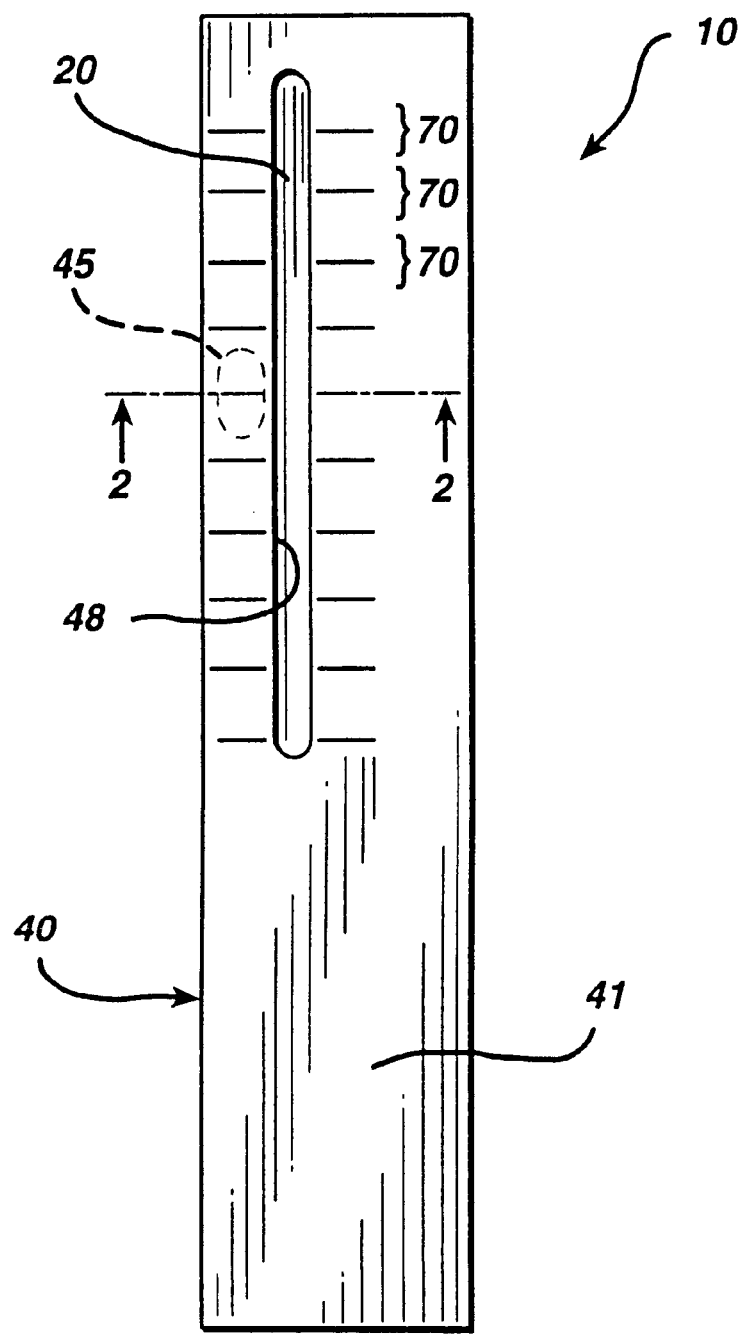
FIG. 1 is an elevation view of a test strip of the present invention.
Figure 2:
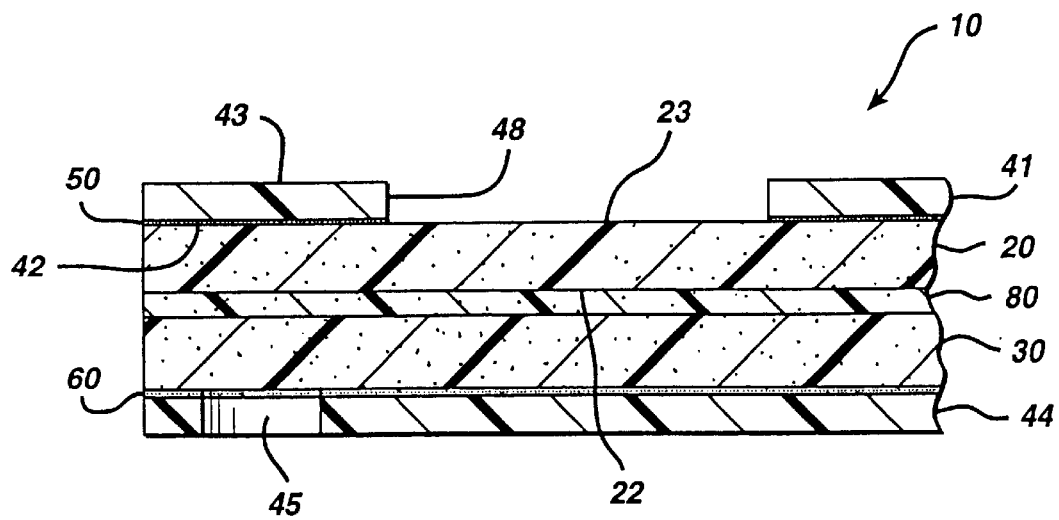
FIG. 2 is a cross-sectional view taken along the plane 2—2 of the test strip of FIG. 1 before compression by a heated shaping die.
Figure 3:
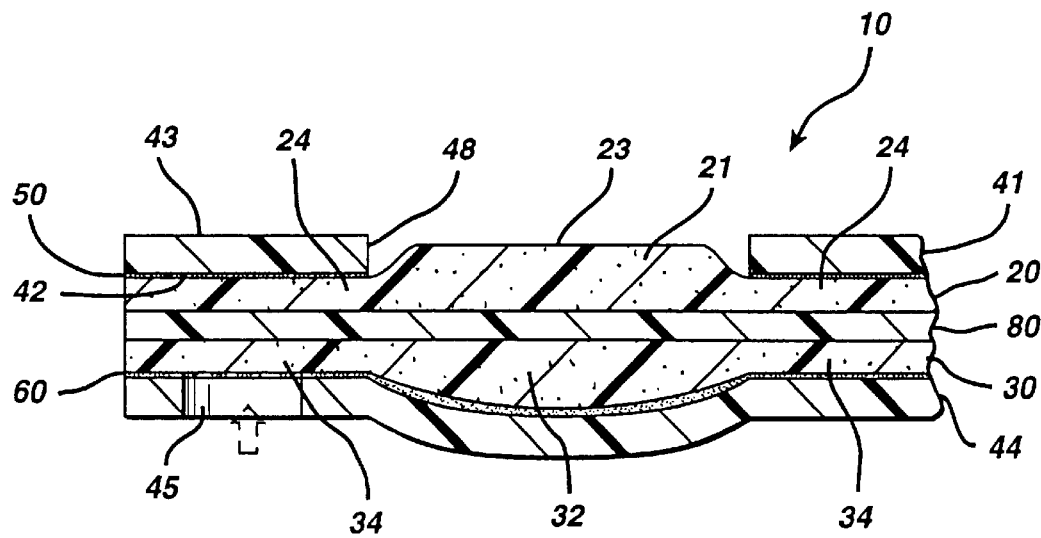
FIG. 3 is the cross-sectional view of FIG. 2 after compression.

A test strip in accordance with the present invention is illustrated in FIG. 1. FIGS. 2 and 3 depict a cross section through the strip of FIG. 1 before and after the strip is compressed, respectively. The test strip 10 comprises a porous membrane 20 having a sample side 22 and a testing side 23, as can be seen in FIGS. 2 and 3. A testing reagent is held within the pores of the membrane. A portion of the membrane is adapted to absorb a body fluid, such as blood, which comes in contact with the sample side 22. The membrane transports the body fluid by capillary action from the sample side 22 toward the testing side 23, where the testing reagent reacts with the analyte to produce a color change. The change in color depends on the concentration of analyte in the sample and enables one to determine the concentration.

Depending on the composition of the testing reagent, the strip can be used to measure analytes such as glucose, cholesterol, proteins, ketones, uric acid, phenylalanine, or enzymes in body fluids such as blood or urine. In a preferred embodiment, the testing reagent includes a component, such as glucose oxidase, for converting glucose (present in a sample of blood) to hydrogen peroxide and components for detecting the hydrogen peroxide produced. The components for detecting hydrogen peroxide may be an oxidizable dye and a peroxidase, such as horseradish peroxidase.

For use with blood samples, it is preferred that the membrane 20 be an anisotropic porous membrane having pores with effective diameters that decrease in size as the distance from the sample side 22 of the membrane increases. As blood is transported through the membrane by capillary action, red blood cells are removed by progressively smaller pores which the blood encounters as it travels. Separation of red blood cells from the blood sample produces a relatively clear fluid through which the change in color near the testing side 23 may be observed.

The thickness of the membrane 20 is usually in the range of about 50 to about 500 micrometers, with a thickness in the range of about 100 micrometers to about 200 micrometers being preferred. For use with blood samples, the membrane 30 preferably has pores with effective diameters in the range of about 5 to about 50 micrometers on the sample side and about 0.1 to about 1.0 micrometers toward the testing side 23. The membrane 10 may be composed of porous polyamides, polysulfones, polyesters, polyolefins, or cellulosics. Polysulfone is the preferred material for the membrane. The testing reagent may be held within the pores of the membrane covalently or non-covalently. When the binding of the testing reagent is intended to be non-covalent, the testing reagent may be, for example, impregnated in the membrane by applying a solution containing the testing reagent to the membrane and subsequently evaporating the solvent.

A porous sheet 30 is in fluid communication with the membrane 20 and is adapted to accept the body fluid sample and transport a detectable portion of the sample to the sample side 22 of the membrane. The sample is absorbed into pores of the porous sheet 30 and passed through the sheet by capillary action. The sheet 30 may be composed of natural fibers, such as cotton or cellulose, as well as polyester, polyamide, polyethylene, polyvinyl alcohol, polyester nylon blends, or other synthetic polymers. Polyester is the preferred material for the porous sheet, with polyester-nylon blends also being favored. The porous sheet 30 is preferably nonwoven, having fibers that are thermally bonded to produce pores having an effective diameter in the range of about 20 to about 200 micrometers, preferably about 50 to 100 micrometers. Its structure provides a venting path for air in the strip that is displaced by the sample, thereby facilitating the passage of sample to the membrane. The sheet is generally intrinsically hydrophilic or rendered hydrophilic by treatment with a surfactant, such as polypropylene glycol.

Preferably, the porous sheet 30 is capable of absorbing and retaining in the range of about 2 to about 10, and more preferably, in the range of about 4 to about 6, times the volume of blood that is required to reliably produce a detectable change in color on the testing side of the membrane. Typically, a minimum of about 3 to about 10 microliters of blood is required for determination of the analyte concentration. Therefore, it is preferred that the porous sheet be capable of absorbing from about 6 to about 100 microliters, ideally about 30 microliters.

Referring now to FIG. 3, the porous sheet 30 includes a pillow portion 32 which retains the major part of body fluids absorbed by the sheet 30, and a relatively compressed portion 34 intended primarily as a sealing and buffer zone extending laterally in opposite directions from the pillow portion.

The strip structure is sandwiched between a cover sheet 41 and a backing sheet 44, which may be of any suitable plastic, but are preferably polyethylene terephthalate. The cover sheet 41 faces the testing side 23 of the membrane and the backing sheet 44 is adjacent to the porous sheet 30. The edges, and optionally the ends, of the strip are sealed by the relatively compressed sealing region 24 of the membrane 20 and the relatively compressed portion 34 of the porous sheet 30 which are sandwiched between the cover sheet 41 and the backing sheet 44. The cover sheet 41 is attached to the membrane 20 by a sealable coating 50 and the backing sheet 44 is fixed to the porous sheet 30 by an adhesive 60. A relatively thin layer of non-woven polyethylene-coated polyester 80 may optionally be positioned between the membrane 20 and the porous sheet 30 to further improve the seal.

An elongated window 48 is cut into the cover sheet, and is in general alignment with the pillow portion 32, exposing a portion of the absorbent region 21 of the membrane. The window permits the testing side 23 of the membrane to be visible and also provides oxygen access to the color-forming reaction in membrane 20. Preferably, the cover sheet 41 is formed of a printable material and colors for comparison or markings dividing the exposed membrane into identifiable zones 70 (shown in FIG. 1) are printed on the cover sheet. The membrane 20 extends across the window 48 and the absorbent region 21 of the membrane may extend into the window, thereby increasing visibility of a color change which may take place near the testing side 23. The pillow portion 32 provides a cushion and support for membrane 20, which is otherwise unsupported in the region where it spans window 48.

Preferably, the membrane also contains an inhibitor which retards the change in color of the testing reagents until a detectable threshold level of glucose is present at the testing side 23. Further, the testing side is divided into zones 70, each having a known concentration of inhibitor and, therefore, a unique but predictable threshold level of glucose. The zones 70 are arranged sequentially along the length of the window 48. Those of the zones 70 that undergo an observable change in color appear to form a continuous line terminating at a definite point along the length of the window 48. Markings printed on the cover sheet allow a user to quickly determine which of the zones 70 have undergone the change in color and determine, within incremental ranges, the concentration of glucose present.

A sample port 45 provides flow communication from the outside of the strip to the porous sheet 30 and to the membrane 20. If the sample port 45 is located in the cover sheet 41, the sample port is in alignment with or adjacent to the absorbent region 21 of the membrane. A body fluid sample that is delivered to the sample port 45 is absorbed by the membrane 20 and any excess fluid is absorbed by the porous sheet 30, which is in fluid communication with the membrane. Alternatively, if the sample port is located in the backing sheet 44, the sample delivered to the sample port passes directly into the porous sheet and an amount of sample needed for analyte concentration determination passes to the membrane by capillary action. Locating the sample port 45 in the backing cover 44 is preferred and is especially preferred in small test strips that require less than a single drop of blood for their operation. In any case, when the membrane is anisotropic, the larger membrane pores are nearer the port. When the port is in the backing cover the larger pores may be near one surface of the membrane (the sample side), the smaller pores near the other surface (the testing side). The advantage of an anisotropic membrane is that the highly-colored red blood cells are captured near the sample side and the serum passes through to the testing side. As a result, there is less interference with the observation (from the testing side) of the color change reaction that measures the analyte concentration. Sheet 30 may be treated with polypropylene glycol or similar surfactants to provide some preliminary blood separation even before the sample reaches membrane 20, which further reduces red cell interference.

If coating 50 is a pressure-sensitive adhesive, heat is not required to seal; the coating is preferably a heat-sealable emulsion-based material. Polyisobutylene rubber and ethylene vinyl acetate are suitable, with ethylene vinyl acetate being preferred. The coating 50 is conveniently applied around or along the face 42 of the cover sheet 41, which is positioned toward the membrane 20. An opposite face 43 is positioned away from the membrane 20.

Alternatively, the adhesive coating 50 may be a low-density polyethylene film that is co-extruded with the polyethylene terephthalate cover sheet on the face 42 of the cover sheet that is positioned toward the membrane. The coating is in the range from about 5 to about 13 micrometers thick if ethylene vinyl acetate is used, and in the range from about 37 to about 87 micrometers thick if co-extruded low-density polyethylene is used. Similarly, the adhesive 60 may be an emulsion-based material such as ethylene vinyl acetate, acrylic, or polyisobutylene. Alternatively, coating 60 may be a pressuresensitive adhesive; however, since coatings 50 and 60 are preferably heat-sealed, in the description that follows heat-sealable coatings are emphasized.

Figure 4:
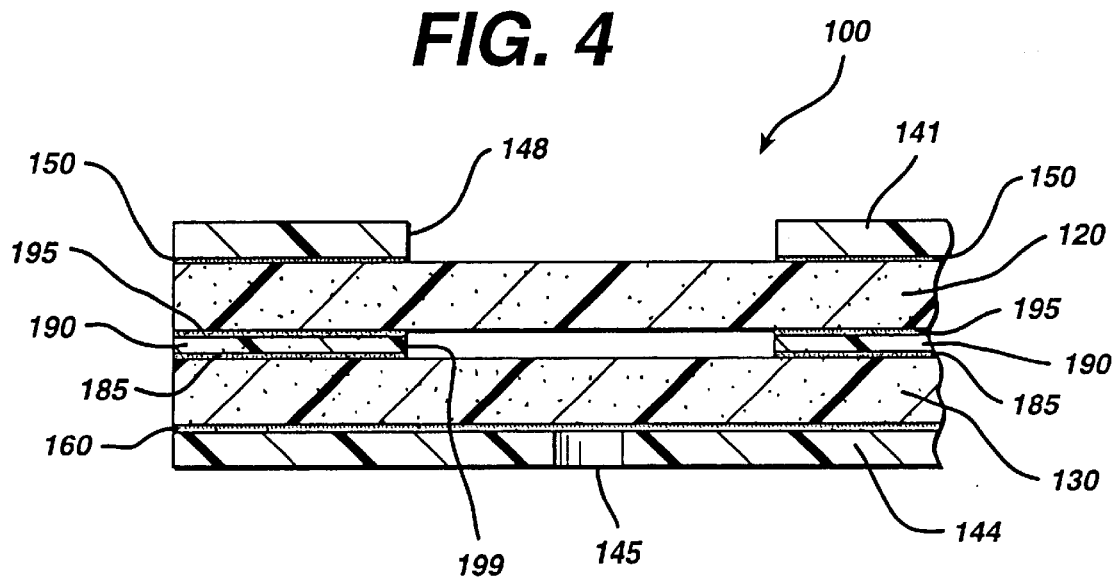
FIG. 4 is the cross-sectional view of a test strip of the present invention that includes an incompressible center plate between an absorbent sheet and a membrane before compression.
Figure 5:
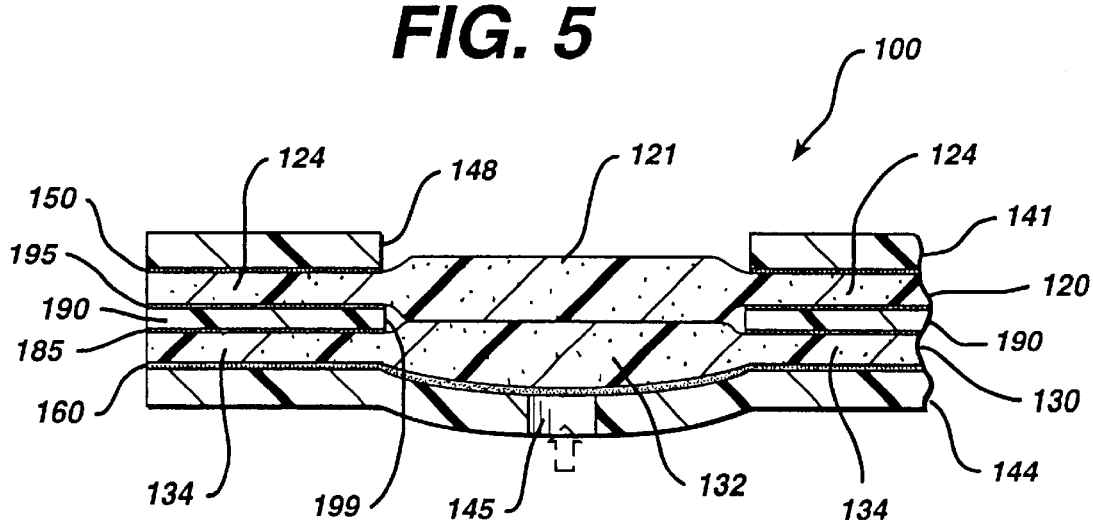
FIG. 5 is the cross-sectional view of FIG. 4 after compression.

Another preferred embodiment in accordance with the present invention is shown in cross section in FIGS. 4 and 5. Each of the numbered elements of FIGS. 4 and 5 that corresponds to a numbered element depicted in FIGS. 1 through 3 is designated by an element number that is one hundred units higher than that of the corresponding element. For example, a membrane 120 in FIG. 4 corresponds to membrane 20. Similarly, an opening 145 corresponds to sample port 45. Elements that have no corresponding element in FIGS. 1 through 3, such as an internal relief chamber 199 illustrated in FIG. 5, are designated by element numbers whose last two digits are freely assigned. Of course, some corresponding elements are not numbered in any of the figures.

Referring now to a test strip 100 illustrated in FIG. 4, a sample port 145 passes through backing sheet 144 for admitting blood or other body fluids. Typically, the backing sheet is rectangular or oblong and is white or clear polyethylene terephthalate, with the opening 145 formed by punching. The backing sheet 144 should be relatively rigid to provide support for the test strip 100. Backing sheet 144 preferably has a thickness in the range from about 25 to about 100 micrometers, with about 50 micrometers preferred. One of the faces of the backing sheet is coated with an adhesive 160, preferably a heat-sealable adhesive as described above, for adhering the sheet to porous absorbent sheet 130.

Alternatively, the backing sheet 144 may be a thermoplastic material, such as a polyvinyl resin, a polystyrene resin, an acrylic resin, a copolymer of ethylene and vinyl acetate, or a mixture of paraffin wax and polyolefins. In that case, no adhesive coating is required to fasten the backing sheet to adjacent porous sheet 130. A combination of heat and pressure serves to partially fuse the thermoplastic material, permitting it to penetrate the porous member. On cooling, a portion of the thermoplastic material solidifies within the porous member, affixing and, optionally, sealing the backing strip 144 to the porous member.

Porous absorbent sheet 130 is adhered to backing sheet 144 and extends across the opening 145. Any liquid that passes through the opening 145 contacts the absorbent sheet 130 and is wicked up by capillary action. Preferably, sheet 130 is a polyester nonwoven material. Material having a weight in the range from about 10 to about 30 grams per square meter has proven satisfactory, with material of about 20 grams per square meter being preferred. The absorbent sheet 130 may be treated with surfactants, such as polypropylene glycol or polyethylene glycol. Preferably, the surfactants are present in the range of about 0.01 to about 5.0 weight percent, based on the total weight of the absorbent sheet 130. Sheet 130 usually has about the same size and shape as the backing sheet 144.

A plastic center plate 190 defines and substantially encircles an internal relief chamber 199. Preferably, the chamber 199 is formed by removing a part of the center plate 190, preferably by punching it out. Adhesive layers, 185 and 195, preferably heat-sealable adhesives, are spread upon the faces of the center plate, either before or after part of the center plate 190 is removed. The adhesive layers are not required when the center plate 190 is a thermoplastic material capable of heat-sealing directly to a porous surface. However, it is currently preferred that the adhesive layers 185 and 195 be employed.

Preferably, the center plate 190 is a polyethylene terephthalate sheet having a thickness in the range of about 50 to about 125 micrometers. A thickness of about 75 micrometers is preferred. Typically, the internal relief chamber 199 is rectangular or oblong, having a length of about 2.5 cm and a width of about 0.1 cm. It is important that the center plate 190 be of a material that is sufficiently incompressible to maintain the dimensions of the internal relief volume substantially unchanged, despite being subjected to conditions effective to compress the absorbent sheet 130 and the membrane 120, and to set the heat-sealable adhesives. Typically, the components are laminated using about 480 to about 860 kPa of pressure at a temperature in the range of about 65° C. to about 110° C. for a period of about 0.5 to about 15 seconds.

The adhesive layer 185 attaches one face of the center plate 190 to the absorbent sheet 130. Adhesive layer 195 attaches the center plate 190 to a relatively broad side of the membrane 120. The membrane 120 is sufficiently permeable to permit liquids, such as body fluids, to pass through relatively freely but solids contained in the liquids, such as red blood cells, may be retained at an external surface of the membrane or at some point within the membrane. The membrane 120 may be anisotropic and is, preferably, a polysulfone that has a thickness in the range of about 100 to about 150 micrometers, preferably about 125 micrometers. The membrane 120 is impregnated with a color-change reagent capable of reacting with an analyte in solution. Very preferably, the reagent contains a component for converting glucose to hydrogen peroxide and an inhibitor, as described above. When the reagent changes color, the external appearance of the membrane 120 is altered.

FIG. 5 shows a cross-sectional view of the elements depicted in FIG. 4 after being compressed and heat-sealed by a heated shaping die. The membrane 120 includes a relatively dense portion 124 which is located adjacent to the center plate 190. The dense portion 124 is formed by the compression and heat-sealing process, and is relatively less permeable to liquids. The membrane 120 also includes an uncompressed portion 121 that is disposed opposite the internal relief chamber 199. During the compression that takes place in the sealing process, portion 124 of the membrane 120 becomes more dense and portion 121 enters into the internal relief chamber 199. The uncompressed portion 121 is relatively permeable to liquids, such as body fluids.

A cover sheet 141, preferably of white or clear translucent plastic is adhered to the side of the membrane 120 that is furthest from the center plate 190. Alternatively, the cover sheet 141 may be a thermoplastic material and attached directly to the membrane 120 by partial fusion and subsequent solidification within the membrane 120. The cover sheet 141 defines a window 148, which has a cross section about the same size and shape as that of the internal relief chamber 199. During compression of the strip, forces that urge the cover sheet 141 in the direction of the center plate 190 tend to cause the uncompressed portion 121 of the membrane 120 to bulge into the internal relief chamber 199 and into the window 148.

Similarly, forces which move the backing plate 144 toward the center plate 190 tend to compress a region 134 of the absorbent sheet 130 which is located between the backing sheet 144 and the center plate 190. In contrast, region 132 of the absorbent sheet 130, which is generally adjacent to the internal relief chamber 199, remains substantially uncompressed and continues to exhibit a relatively high degree of absorbency. During compression, membrane 120 and/or absorbent sheet 130 may buckle, causing the two layers to come into physical contact.

Figure 6:
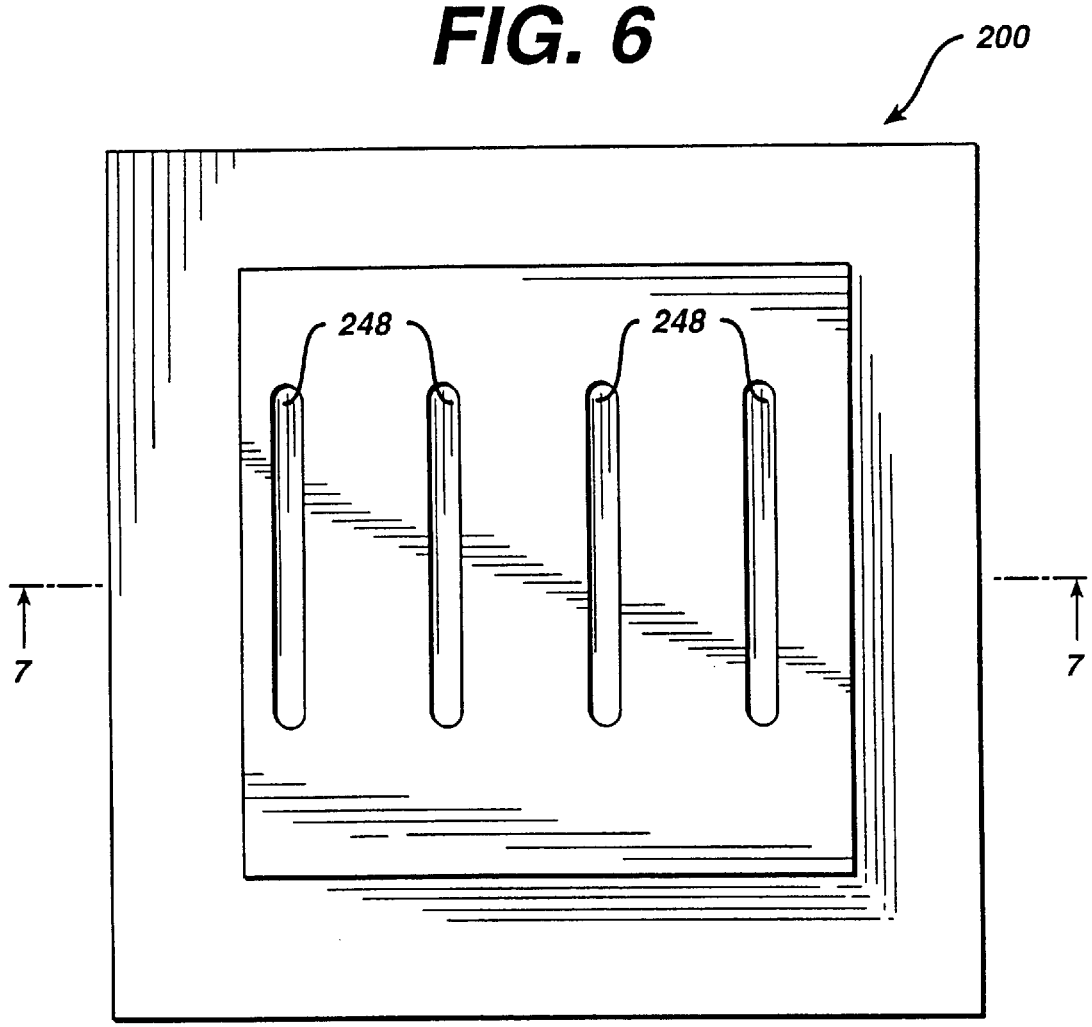
FIG. 6 is an elevation view of a shaping die that can be used in the method of the present invention.
Figure 7:
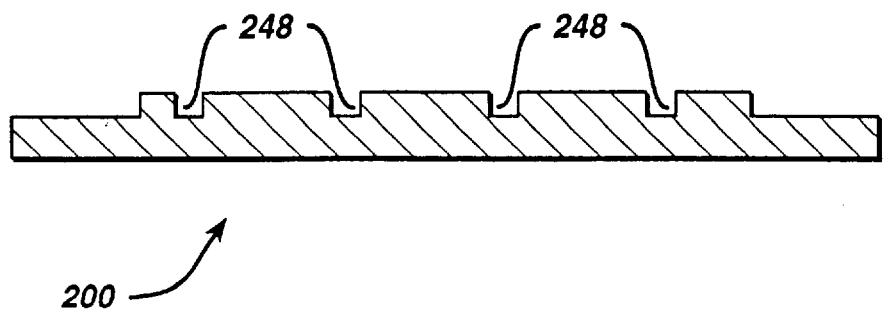
FIG. 7 is a cross-sectional view taken along the plane 7—7 of the die of FIG. 6.

FIG. 6 depicts the face of a die 200 that is used to compress the strip of FIG. 2 (or FIG. 4) to the configuration shown in FIG. 3 (or FIG. 5). FIG. 7 is a cross-sectional view taken along the plane 7—7 on FIG. 6. The compression step is accomplished by sandwiching strip material between the die of FIG. 6 and a flat plate and applying pressure. Preferably, the die is also heated. The die shown forms four strips; however, it is clear that more or fewer strips may be formed at one time by suitably modifying the die. The method for compressing the strip material is described in greater detail as follows. Although described with reference to FIGS. 2 and 3, the method is similarly suited for making the embodiment of the test strip depicted in FIGS. 4 and 5. The method comprises assembling the cover sheet 41, sealable coating 50, membrane 20, polyethylene-coated polyester layer 80, porous sheet 30, adhesive 60, and backing sheet 44 in their proper orientation (described above) as a sealable package on a shaping die of FIG. 6 that is preferably heated. FIG. 2 provides a cross section of the configuration before heat or pressure is applied. As shown in FIG. 6, the die has a substantially flat surface which has at least one elongated groove 248 (4 grooves in FIG. 6) having a length about equal to or greater than the length of the window 48 (FIG. 1). The sealable package is positioned on the die with the groove and window in alignment, so that pressing the package against the die will shape the porous sheet 30 into a pillow portion 32 adjacent the membrane 20 and urge the membrane 20 into the window 48.

The sealable package is pressed between the die and a flat plate. Portions of the membrane 20 and of porous sheet 30, located on opposite sides of the groove adjacent to flat surfaces of the die, are compressed and become relatively impermeable to body fluids, producing the relatively compressed regions 24 and 34. Preferably, in addition, heat from the die causes the (heat-sealable) coating 50 to bond to the cover sheet 41 and to the membrane 20. The heat also causes the adhesive 60 to bond to the porous layer 30 and the backing sheet 44. A pressure in the range of about 340 to about 1400 kPa, preferably about 480 to about 860 kPa, is applied to the materials by the die while the die is preferably heated to a temperature in the range of about 65° C. to about 110° C.

Descriptions of the invention and examples of its use have been set forth to communicate the invention fully, not to limit the scope of the invention in any way. It should now be apparent that other forms and embodiments of the invention are possible. The scope of the invention is intended to be as broad as the claims will allow.

We claim:

1. A test strip, for determining the concentration of an analyte in a body fluid, which comprises:
   a cover sheet, having an elongated window cut through it;
   a lamellar membrane adjacent to the cover sheet, extending across and into the window and containing a reagent that reacts with the analyte to produce a color change;
   a porous sheet in fluid communication with the membrane, having a porous, enlarged pillow portion and a compressed portion, the pillow portion being substantially aligned with the window; and
   a backing sheet, adjoining the porous sheet and having a sample port cut through it;
   whereby fluid introduced into the sample port can flow through the porous sheet to the membrane, and analyte in the fluid can react with the reagent to produce a color change visible through the window.

2. The test strip of claim 1 wherein the analyte is glucose and the body fluid is blood.

3. The test strip of claim 1 wherein the cover sheet comprises polyethylene terephthalate.

4. The test strip of claim 1 wherein the backing sheet comprises polyethylene terephthalate.

5. The test strip of claim 1 wherein the membrane is anisotropic, having relatively larger pores nearer the sample port and smaller pores near the window and cover sheet.

6. The test strip of claim 1 wherein the membrane contains a plurality of zones with various predetermined concentrations of an inhibitor for the analyte-reagent reaction.

7. The test strip of claim 1 wherein the porous sheet comprises a nonwoven material.

8. The test strip of claim 7 wherein the nonwoven material is a polyester or a polyester-polyamide blend.

9. The test strip of claim 1 wherein the pillow region can absorb about 6 to about 100 microliters of human blood.

10. The test strip of claim 9 wherein the pillow region can absorb about 30 microliters of human blood.

11. The test strip of claim 1 wherein the membrane can absorb about 8 to about 10 microliters of human blood.

12. The test strip of claim 1 wherein the cover sheet is attached to the membrane with a heat-sealable adhesive.

13. The test strip of claim 12 wherein the adhesive comprises polyisobutylene rubber or ethylene vinyl acetate.

14. The test strip of claim 13 wherein the adhesive comprises ethylene vinyl acetate.

15. The test strip of claim 12 wherein the adhesive is a low-density polyethylene co-extruded with the cover sheet.

16. The test strip of claim 1 wherein the porous sheet contains polypropylene glycol in an amount effective as a surfactant to improve wicking of fluid by the porous sheet.

17. The test strip of claim 1 wherein a nonwoven layer of polyethylene-coated polyester is located between the membrane and the porous sheet.

* * * * *